US010441822B2

(12) United States Patent
Buckley et al.

(10) Patent No.: US 10,441,822 B2
(45) Date of Patent: Oct. 15, 2019

(54) SKINCARE COMPOSITIONS

(71) Applicant: Reckitt Benckiser Healthcare International Limited, Slough (GB)

(72) Inventors: Carolyn Buckley, Hull (GB); Stuart Jackson, Hull (GB); Neil Kilcullen, Hull (GB); Diane Marie Pavis, Hull (GB)

(73) Assignee: RECKITT BENCKISER HEALTHCARE INTERNATIONAL LIMITED, Slough (GB)

( * ) Notice: Subject to any disclaimer, the term of this patent is extended or adjusted under 35 U.S.C. 154(b) by 0 days.

(21) Appl. No.: 15/988,595

(22) Filed: May 24, 2018

(65) Prior Publication Data

US 2018/0264292 A1 Sep. 20, 2018

Related U.S. Application Data

(63) Continuation of application No. 13/384,233, filed as application No. PCT/GB2010/051170 on Jul. 19, 2010, now Pat. No. 10,065,052.

(30) Foreign Application Priority Data

Jul. 17, 2009 (GB) .................................. 0912481.9

(51) Int. Cl.
*A61Q 19/00* (2006.01)
*A61K 8/02* (2006.01)
*A61K 8/34* (2006.01)
*A61K 8/365* (2006.01)
*A61K 8/368* (2006.01)
*A61K 8/44* (2006.01)
*A61K 8/49* (2006.01)
*A61K 8/60* (2006.01)
*A61K 8/63* (2006.01)
*A61K 8/67* (2006.01)
*A61K 8/97* (2017.01)
*A61K 9/00* (2006.01)
*A61K 31/045* (2006.01)
*A61K 31/19* (2006.01)
*A61K 31/4166* (2006.01)
*A61K 31/60* (2006.01)
*A61K 36/185* (2006.01)
*A61K 45/06* (2006.01)

(52) U.S. Cl.
CPC .......... *A61Q 19/008* (2013.01); *A61K 8/0208* (2013.01); *A61K 8/34* (2013.01); *A61K 8/365* (2013.01); *A61K 8/368* (2013.01); *A61K 8/442* (2013.01); *A61K 8/4913* (2013.01); *A61K 8/4946* (2013.01); *A61K 8/602* (2013.01); *A61K 8/63* (2013.01); *A61K 8/675* (2013.01); *A61K 8/97* (2013.01); *A61K 9/0014* (2013.01); *A61K 31/045* (2013.01); *A61K 31/19* (2013.01); *A61K 31/4166* (2013.01); *A61K 31/60* (2013.01); *A61K 36/185* (2013.01); *A61K 45/06* (2013.01); *A61Q 19/00* (2013.01); *A61K 2800/28* (2013.01)

(58) Field of Classification Search
CPC .. A61K 2300/00; A61K 31/60; A61K 8/4946; A61K 9/0014; A61Q 19/008
See application file for complete search history.

(56) References Cited

U.S. PATENT DOCUMENTS

| 5,482,710 | A | * | 1/1996 | Slavtcheff | ............ A61K 8/0212 424/65 |
|---|---|---|---|---|---|
| 5,520,919 | A | | 5/1996 | Lerner | |
| 5,558,071 | A | | 9/1996 | Ward et al. | |
| 5,843,998 | A | | 12/1998 | Song et al. | |
| 6,071,541 | A | * | 6/2000 | Murad | ...................... A61K 8/22 424/616 |
| 6,579,851 | B2 | | 6/2003 | Goeke et al. | |
| 8,263,097 | B2 | | 9/2012 | Jitpraphai et al. | |
| 8,461,129 | B2 | | 6/2013 | Bolduc et al. | |
| 2001/0019722 | A1 | | 9/2001 | Fotinos et al. | |
| 2002/0054918 | A1 | | 5/2002 | Murad | |
| 2003/0180334 | A1 | | 9/2003 | Zhou et al. | |
| 2006/0165644 | A1 | * | 7/2006 | Tanaka | ..................... A61K 8/97 424/74 |
| 2007/0224231 | A1 | * | 9/2007 | Schmidt | ............... A61K 8/0208 424/402 |
| 2008/0044494 | A1 | * | 2/2008 | Robinson | ................. A61K 8/06 424/684 |
| 2009/0148391 | A1 | * | 6/2009 | Schmaus | ................ A61K 8/347 424/59 |
| 2011/0028412 | A1 | | 2/2011 | Cappello et al. | |
| 2013/0084243 | A1 | | 4/2013 | Goetsch et al. | |
| 2013/0096073 | A1 | | 4/2013 | Sidelman | |

FOREIGN PATENT DOCUMENTS

| EP | 2380657 A1 | * | 10/2011 | ............... A61K 8/06 |
|---|---|---|---|---|
| EP | 2380657 A1 | | 10/2011 | |
| GB | 2076286 A | | 12/1981 | |
| JP | H09500889 A | | 1/1997 | |
| JP | 2003530302 A | | 10/2003 | |
| JP | 2009522337 A | | 6/2009 | |
| WO | 2010058853 A1 | | 5/2010 | |

OTHER PUBLICATIONS

Third Party Observation under Art 115 of EPC in related EP Publication No. EP2528577 dated Oct. 1, 2014.
(Continued)

*Primary Examiner* — Andrew S Rosenthal
(74) *Attorney, Agent, or Firm* — Troutman Sanders LLP; Ryan Schneider; Chris Davis

(57) ABSTRACT

This invention relates to skincare compositions, in particular compositions effective in the treatment of acne vulgaris, and to methods of treatment of the skin that involve the application of such compositions, wherein the compositions comprise salicylic acid or a salt thereof in combination with at least two actives selected from the group consisting of lactic acid or a salt thereof; glycyrrhizinic acid or a salt or a derivative thereof; bisabolol; cetylhydroxyproline palmitamide; allantoin; niacinamide; and *Epilobium angustifolium* extract.

14 Claims, No Drawings

(56) References Cited

OTHER PUBLICATIONS

Gehring, W., "Nicotinic Acid/Niacinamide and the Skin," Journal of Cosmetic Dermatology, 2004, 88-93, 3 (abstract only).
Barrett et al. (http://www.chelationwatch.org/reg/fda_warning.shtml), Sep. 26, 2008.
"Viscosity" (http://www.viscopedia.com/basics/factors-affecting-viscometry/) access Jan. 5, 2018, pp. 1-6 (Year: 2018).
"PH" (http://phadjustment.com/ph.html) accessed Jan. 5, 2018, pp. 1-7 (Year: 2018).
"Emulsion" (http://www.molecularrecipes.com/emulsions/emulsion-types/) accessed Jan. 5, 2018, pp. 1-7 (Year: 2018).

* cited by examiner

SKINCARE COMPOSITIONS

CROSS-REFERENCE TO RELATED APPLICATIONS

This application is a continuation application of U.S. patent application Ser. No. 13/384,233, filed 2 Mar. 2012, which is a U.S. National Stage of International Application No. PCT/GB2010/051170, filed 19 Jul. 2010, which claims the benefit of GB 0912481.9, filed 17 Jul. 2009, all of which are herein fully incorporated by reference.

FIELD OF THE INVENTION

This invention relates to skincare compositions, in particular compositions effective in the treatment of acne vulgaris, and to methods of treatment of the skin that involve the application of such compositions.

BACKGROUND OF THE INVENTION

Acne vulgaris (acne) is a chronic inflammatory condition of the pilosebaceous units of the skin, which is particularly prevalent in adolescents. The condition generally causes the formation, on the skin, of comedones, red papules, pustules and sometimes cysts. This is unsightly and furthermore, if untreated, acne can lead to scarring of the skin. The major causes of acne are thought to be an increase in sebum production, an increased presence of *Propionibacterium acne* (*P. acne*), blockage of the pilosebaceus duct and the production of inflammation.

Salicylic acid is known to be effective in the treatment of acne. It is a topical keratolytic agent that works by dissolving the intercellular cement that holds epithelial cells together. Salicylic acid is used in a variety of over-the-counter acne remedies.

In order to improve the efficacy of topical acne treatments, it is desired to formulate salicylic acid with one or more control agents to regulate the inflammatory effects sometimes observed, such as local skin peeling and discomfort such as burning and skin reddening.

Surprisingly, it has now been found that skincare compositions comprising salicylic acid and at least two or more chosen actives have improved therapeutic efficacy in the treatment of acne. Said skincare compositions have both the ability to treat acne and reduce the appearance of redness on the skin.

BRIEF SUMMARY OF THE INVENTION

Thus, according to a first aspect of the invention there is provided a skincare composition suitable for topical application to the skin, the composition comprising salicylic acid or a salt thereof, combined with at least 2 actives selected from the group consisting of: lactic acid or a salt thereof; glycyrrhizinic acid or a salt or derivatives thereof, bisabolol; cetylhydroxyproline palmitamide; allantoin; niacinamide; and, Canadian Willowherb (*Epilobium angustifolium*) extract.

In another aspect, the disclosure provides for a cosmetic method for improving the appearance of skin afflicted by acne lesions, said method comprising reducing the redness of said lesions by the topical application of a skincare composition comprising a keratolytic agent in combination with at least two actives selected from the group consisting of: lactic acid or a salt thereof; glycyrrhizinic acid or a salt or derivative thereof, bisabolol; cetylhydroxyproline palmitamide; allantoin; niacinamide; and, *Epilobium angustifolium* extract.

In another aspect, the disclosure provides for a method for reducing irritancy associated with the topical application of a skincare composition comprising salicylic acid in combination with at least two actives selected from the group consisting of lactic acid or a salt thereof; glycyrrhizinic acid or a salt or derivative thereof; bisabolol; cetylhydroxyproline palmitamide; allantoin; niacinamide; and *Epilobium angustifolium* extract.

In some embodiments of any of the methods herein, the keratolytic agent comprises salicylic acid or a salt thereof. In some embodiments, the concentration of salicylic acid or a salt thereof is at least 0.01 percent by weight. In some embodiments of any of the methods herein, the concentration of salicylic acid or a salt thereof is less than 10 percent by weight.

In some embodiments of any of the methods herein, one of the actives comprises lactic acid or a salt thereof. In some embodiments of any of the methods herein, the concentration of lactic acid or a salt thereof is at least 0.01 percent by weight. In some embodiments of any of the methods herein, the concentration of lactic acid or a salt thereof is less than 10 percent by weight.

In some embodiments of any of the methods herein, one of the actives comprises glycyrrhizinic acid or a salt or derivative thereof. In some embodiments of any of the methods herein, the concentration of the glycyrrhizinic acid or a salt or derivative thereof is at least 0.01 percent by weight. In some embodiments of any of the methods herein, the concentration of glycyrrhizinic acid or a salt or derivative thereof is less than 2 percent by weight.

In some embodiments of any of the methods herein, one of the actives comprises bisabolol. In some embodiments of any of the methods herein, the concentration of bisabolol is at least 0.001 percent by weight. In other embodiments of any of the methods herein, the concentration of bisabolol is less than 1 percent by weight.

In some embodiments of any of the methods herein, one of the actives comprises cetylhydroxyproline palmitamide. In some embodiments of any of the methods herein, the concentration of cetylhydroxyproline palmitamide is at least 0.001 percent by weight. In some embodiments of any of the methods herein, the concentration of cetylhydroxyproline palmitamide is less than 1 percent by weight.

In some embodiments of any of the methods herein, one of the actives comprises allantoin. In some embodiments of any of the methods herein, the concentration of allantoin is at least 0.01 percent by weight. In some embodiments of any of the methods herein, the concentration of allantoin is less than 5 percent by weight.

In some embodiments of any of the methods herein, one of the actives comprises niacinamide. In some embodiments of any of the methods herein, the concentration of niacinamide is at least 0.01 percent by weight. In some embodiments of any of the methods herein, the concentration of niacinamide is less than 10 percent by weight.

In some embodiments of any of the methods herein, one of the actives comprises *Epilobium angustifolium*. In some embodiments of any of the methods herein, the concentration of *Epilobium angustifolium* is at least 0.001 percent by weight. In some embodiments of any of the methods herein, the concentration of *Epilobium angustifolium* is less than 1 percent by weight.

In some embodiments of any of the methods herein, the keratolytic agent comprises 0.1 to 5 wt % salicylic acid or a salt thereof, and the at least two actives are selected from the group consisting of: 0.1 to 5 wt % lactic acid or a salt thereof; 0.01 to 1 wt % glycyrrhizinic acid or a salt or derivative thereof; 0.001 to 1 wt % bisabolol; 0.001 to 1 wt % cetylhydroxyproline palmitamide; 0.1 to 2 wt % allantoin; 0.1 to 5 wt % niacinamide; and, 0.001 to 1% *Epilobium angustifolium* extract.

In some embodiments of any of the methods herein, the keratolytic agent comprises 1 to 3 wt % salicylic acid or a salt thereof, and the at least two actives are selected from the group consisting of: 1 to 3 wt % lactic acid or a salt thereof; 0.01 to 0.5 wt % glycyrrhizinic acid or a salt or derivative thereof; 0.02 to 0.5 wt % bisabolol; 0.01 to 0.5 wt % cetylhydroxyproline palmitamide; 0.2 to 1 wt % allantoin; 0.5 to 5 wt % niacinamide; and, 0.01 to 0.5% *Epilobium angustifolium* extract.

In some embodiments of any of the methods herein, the pH is in the range from 3.5 to 6.0.

In some embodiments of any of the methods herein, the skincare composition further comprises one or more further topically active skincare agents selected from the group consisting of an antimicrobial or anti-bacterial compound, an anti-viral compound, an anti-fungal compound, an anti-inflammatory compound, and an anthelmintic compound.

In some embodiments of any of the methods herein, the skincare composition has the form of one of an aqueous solution surfactant wash, an oily solution surfactant wash, a dispersion, an emulsion, or a gel. In some embodiments of any of the methods herein, the skincare composition has the form of an emulsion selected from the group consisting of an oil-in-water emulsion, a water-in-oil emulsion, and a microemulsion. In some embodiments of any of the methods herein, the skincare composition has the form of an emulsion comprising an oil-in-water emulsion. In some embodiments of any of the methods herein, the skincare composition has the form of a gel comprising an aqueous gel.

In some embodiments of any of the methods herein, the skincare composition further comprises one or both of a gelling and a thickening agent.

In some embodiments of any of the methods herein, the skincare composition further comprises an aqueous solvent system. In some embodiments of any of the methods herein, the aqueous solvent system is a mixed solvent system comprising water in admixture with a co-solvent. In some embodiments of any of the methods herein, the co-solvent is an alcohol.

In some embodiments of any of the methods herein, the skincare composition further comprises one or more excipients selected from the group consisting of emulsifiers, emollients, lipids, humectants or moisturizers, binders, conditioning agents, emulsion stabilizing salts, preservatives, chelating agents, sequestering agents, abrasives, pH adjusters, surfactants, perfumes and colorings.

In some embodiments of any of the methods herein, the step of applying the skincare composition to the skin comprises the use of a fibrous substrate impregnated with the skincare composition. In some embodiments of any of the methods herein, the fibrous substrate is selected from the group consisting of cellulose fibers, cotton fibers, and a mixture thereof.

It has been found that this treatment provides advantages over existing acne treatments, particularly in tolerance of the acne treatment by the skin. It may have an effect in reducing the severity of the acne and hence any associated marks or scarring that can occur; furthermore, cutaneous irritation may be reduced. Other measures indicating advantages are the reduction in inflammation in the affected skin and/or a soothing effect. A synergistic association between the chosen combination of ingredients may provide that a composition may have lesser amounts of each individual ingredient Salicylic acid is preferably incorporated into the composition according to the invention as the free acid. However, the pH of the composition may, and generally will, be such that the salicylic acid exists in the composition in dissociated form. As the composition may well contain cationic counterions, the salicylic acid may then be thought of as being present in salt form. Alternatively, the salicylic acid may be incorporated into the composition already in salt form, e.g., as a salt with a Group I metal, such as sodium salicylate. As used herein, unless the context requires otherwise, any and all references to salicylic acid should be taken to encompass references to the acid and to dissociated forms and salts thereof.

The concentration of salicylic acid in the composition according to the invention is preferably at least 0.01 percent by weight, more preferably at least 0.1 percent, most preferably at least 0.5 percent and especially at least 1 percent by weight. The concentration of salicylic acid is preferably less than 10 percent, more preferably less than 5 percent, most preferably less than 4 percent and especially less than 3 percent by weight. The concentration of salicylic acid may therefore fall in the range 0.01 percent to 10 percent by weight, more preferably 0.1 percent to 5 percent, and most preferably 0.5 percent to 4 percent and especially 1 to 3 percent by weight. A particularly preferred concentration of salicylic acid is 2 percent by weight.

The concentration of lactic acid or salt thereof when present in the composition is at least 0.01 percent by weight, more preferably at least 0.1 percent by weight and most preferably at least 1 percent by weight; and is less than 10 percent by weight, more preferably less than 5 percent by weight, and most preferably less than 3 percent by weight.

The concentration of glycyrrhizinic acid or a salt or a derivative thereof when present in the composition is at least 0.01 percent by weight and is less than 2 percent by weight, more preferably less than 1 percent by weight, and most preferably less than 0.5 percent by weight.

The concentration of bisabolol when present in the composition is at least 0.001 percent by weight, more preferably at least 0.01 percent by weight and is less than 1 percent by weight, more preferably less than 0.5 percent by weight, The concentration of cetylhydroxyproline palmitamide when present in the composition is at least 0.001 percent by weight, more preferably at least 0.01 percent by weight and is less than 1 percent by weight, more preferably less than 0.5 percent by weight.

The concentration of allantoin when present in the composition is at least 0.01 percent by weight, more preferably at least 0.1 percent by weight and most preferably at least 0.2 percent by weight, and is less than 5 percent by weight, more preferably less than 2 percent by weight, and most preferably less than 1 percent by weight.

The concentration of niacinamide when present in the composition is at least 0.01 percent by weight, more preferably at least 0.1 percent by weight and most preferably at least 0.5 percent by weight, and is less than 10 percent by weight, more preferably less than 5 percent by weight.

The concentration of *Epilobium angustifolium* extract when present in the composition is at least 0.01 percent by weight, and is less than 5 percent by weight, more preferably less than 1 percent by weight, and most preferably less than 0.5 percent by weight.

DETAILED DESCRIPTION OF PREFERRED EMBODIMENTS

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

In a particularly preferred embodiment of the present invention, there is provided a skincare composition comprising 0.1 to 5 wt % salicylic acid, or a salt thereof, in combination with at least 2 actives selected from the group consisting of: 0.1 to 5 wt % lactic acid or a salt thereof; 0.01 to 1 wt % glycyrrhizinic acid or a salt or derivative thereof; 0.001 to 1 wt % bisabolol; 0.001 to 1 wt % cetylhydroxyproline palmitamide; 0.1 to 2 wt % allantoin; 0.1 to 5 wt % niacinamide; and, 0.001 to 1% *Epilobium angustifolium* extract.

In a further particularly preferred embodiment of the present invention, there is provided a skincare composition comprising 1 to 3 wt % salicylic acid or a salt thereof; in combination with at least 2 actives selected from the group consisting of: 1 to 3 wt % lactic acid or a salt thereof; 0.01 to 0.5 wt % glycyrrhizinic acid or a salt or derivative; 0.02 to 0.5 wt % bisabolol; 0.01 to 0.5 wt % cetylhydroxyproline palmitamide; 0.2 to 1 wt % allantoin; 0.5 to 5 wt % niacinamide; and, 0.01 to 0.5% *Epilobium angustifolium* extract.

The composition is preferably prepared with a pH in the range 2.5 to 8.0, more preferably 3.0 to 7.0, and particularly a pH in the range 3.5 to 6.0, e.g., about pH 4.5 or pH 5.5.

A composition according to the invention may comprise one or more further topically active ingredients useful in skincare. Such active ingredients may include one or more of the following:

antimicrobial or antibacterial compounds, for example selected from the following: triclosan, neomycin, clindamycin, polymyxin, bacitracin, benzoyl peroxide, hydrogen peroxide, tetracylines such as doxycycline or minocycline, sulfa drugs such as sulfacetamide, penicillins, cephalosporins such as cephaiexin, and quinolones such as lomefloxacin, olfoxacin or trovafloxacin;

antiviral compounds, for example selected from acyclovir, tamvir, and penciclovir;

antifungal compounds, for example selected from the following: famesol, clotrimazole, ketoconazole, econazole, fluconazole, calcium or zinc undecylenate, undecylenic acid, butenafine hydrochloride, ciclopirox olaimine, miconazole nitrate, nystatin, sulconazole, and terbinafine hydrochloride; anti-inflammatory compounds, for example selected from the following: steroidal agents selected from hydrocortisone, fluocinolone acetonide, halcinonide, halobetasol propionate, clobetasol propionate, betamethasone dipropionate, betamethasone valerate, and triamcinolone acetonide, and non-steroidal anti-inflammatory agents selected from aspirin, ibuprofen, ketoprofen, naproxen, aloe vera gel, aloe vera, licorice extract, pilewort or zinc;

anthelmintic compounds, for example metronidazole.

The composition according to the invention may be formulated in numerous forms. However, the composition may often take the form of an aqueous or oily solution or surfactant wash or dispersion or emulsion or a gel. An emulsion may be an oil-in-water emulsion, or a water-in-oil emulsion, or microemulsion.

The oil phase of emulsions may comprise, but are not exclusive to: hydrocarbon oils such as paraffin or mineral oils; b) waxes such as beeswax or paraffin wax; c) natural oils such as sunflower oil, apricot kernel oil, shea butter or jojoba oil; d) silicone oils such as dimethicone, cyclomethicone or cetyldimethicone; e) fatty acid esters such as isopropyl palmitate, isopropyl myristate, dioctylmaleate, glyceryl oleate and cetostearyl isononanoate; f) fatty alcohols such as cetyl alcohol or stearyl alcohol and mixtures thereof (e.g., cetearyl alcohol); g) polypropylene glycol or polyethylene glycol ethers, e.g., PPG-14 butyl ether; or h) mixtures thereof, for example, the blend of waxes available commercially under the trade name Cutina (Henkel).

Emulsifiers used may be any emulsifiers known in the art for use in water-in-oil or oil-in-water emulsions or microemulsions. Known cosmetically acceptable emulsifiers may include: a) sesquioleates such as sorbitan sesquioleate, available commercially for example under the trade name Arlacel 83 (ICI), or polyglyceryl-2-sesquioleate; b) ethoxylated esters of derivatives of natural oils such as the polyethoxylated ester of hydrogenated castor oil available commercially for example under the trade name Arlacel 989 (ICI); c) silicone emulsifiers such as silicone polyols available commercially for example under the trade name ABIL WS08 (Th. Goldschmidt AG); d) anionic emulsifiers such as fatty acid soaps e.g., potassium stearate and fatty acid sulphates e.g., sodium cetostearyl sulphate available commercially under the trade name Dehydag (Henkel); e) ethoxylated fatty alcohols, for example the emulsifiers available commercially under the trade name Brij (ICI); sorbitan esters, for example the emulsifiers available commercially under the trade name Span (ICI); g) ethoxylated sorbitan esters, for example the emulsifiers available commercially under the trade name Tween (ICI); h) ethoxylated fatty acid esters such as ethoxylated stearates, glyceryl monostearates for example the emulsifiers available commercially under the trade name Myrj (ICI); i) ethoxylated mono-, di-, and triglycerides, for example the emulsifiers available commercially under the trade name Labrafil (Alfa Chem.); j) non-ionic self-emulsifying waxes, for example the wax available commercially under the trade name Polawax (Croda); k) ethoxylated fatty acids, for example, the emulsifiers available commercially under the trade name Tefose (Alfa Chem.); l) methylglucose esters such as polyglycerol-3 methyl glucose distearate available commercially under the name Tegocare 450 (Degussa Goldschmidt); m) as well as polyacrylamide emulsifier systems for examples cream gel emulsifier under trade name Sepigel 305 (Seppic) or n) mixtures thereof.

Gels provided according to the invention may be aqueous or non-aqueous. Aqueous gels are preferred. The gel will contain a gelling agent(s) in order to give sufficient viscosity to the gel. Suitable gelling agents may be hydroxypropyl guar or a copolymer of acryloyl dimethyl tauric acid (or a salt thereof), especially a copolymer of that monomer with another vinylic monomer. The salt may be a salt of a Group I alkali metal, but is more preferably an ammonium salt. Examples of suitable copolymer gelling agents are ammonium acryloyl dimethyl taurate/vinyl pyrrolidone copolymer, ammonium acryloyl dimethyl taurate/Beheneth-25 methacrylate copolymer, ammonium acryloyldimethyltaurate/vinyl formamide copolymer These materials are available from Clariant GmbH in the range of products under the trade name Aristoflex.

A variety of thickening agents may also be used according to the nature of the liquid carrier and the viscosity required. Thickeners that are water-soluble or hydrophilic are preferred, and examples include acrylic acid polymers, e.g., those available commercially under the trade name Carbopol (B.F. Goodrich), modified celluloses, e.g., hydroxypropylmethylcellulose or hydroxyethylcellulose available commercially under the trade name Natrosol (Hercules), alkylgalactomanans available under the trade name N-Hance, xanthan gum, cetyl alcohol and sodium chloride.

The amount of gelling and/or thickening agent in the composition will each preferably lie in the range 0.1 to 5 percent w/w, more preferably 0.5 to 5 percent w/w. Typically, the amount of gelling and/or thickening agent will each be less than 3 percent w/w, e.g., about 1 percent w/w or about 2 percent w/w.

The composition according to the invention preferably has a viscosity of from about 10,000 mPa·s to about 200,000 mPa·s. Viscosity may be measured using a Brookfield RVT viscometer equipped with a T bar C rotating at 5 rpm for 1 minute.

In many instances, it is preferred that the composition should comprise a chelating or sequestering agent, or other agent capable of complexation or other interaction with metal ions present in the composition. Such agents may improve the stability of the composition, and in particular may inhibit or prevent degradation of several ingredients (e.g., fragrance). Examples of chelating or sequestering agents include ethylenediamine tetraacetic acid and its salts, notably the dipotassium and especially the disodium salt.

In the case of solutions or dispersions, and gels, the composition will generally contain a solvent system or other continuous liquid phase. Such a system is preferably aqueous. However, mixed solvent systems may often be used with advantage. Such a mixed solvent system most preferably comprises water, in admixture with a co-solvent, most preferably a lower (e.g., $C_{1-6}$) alcohol, in particular ethanol and t-butyl alcohol.

Preferred aqueous systems comprise water in an amount of at least 25 percent by weight, more preferably at least 35 percent by weight. The upper limit of water will depend on the amounts of other ingredients incorporated in the composition so that the water may form the remainder of the composition up to 100 percent of the composition.

The composition may additionally comprise other components which will be well known to those skilled in the art. These include, for example:

a) Emollients—ingredients that help to maintain the soft, smooth and pliable appearance of skin. Such ingredients may function by their ability to remain on the surface of the skin or in the stratum corneum, and to act as lubricants, reducing or preventing flaking of the skin and improving the skin's appearance. Examples of emollients are isopropyl myristate, triglycerides of fatty acids e.g., lauric triglyceride or capric/caprylic triglyceride, such as the triglyceride available commercially under the trade name Miglyol 810 (Huls UK), and the polypropylene glycol ether of stearyl alcohol known as PPF-15 Stearyl Ether. Particularly preferred emollients are octyldodecanol and polysiloxane compounds, in particular those known as dimethicones.

b) Humectants or Moisturisers—ingredients intended to increase the water content of the top layers of the skin. Examples of such ingredients are glycerin, sorbitol, 1,3-butylene glycol and propylene glycol.

c) Surfactants—Surfactants may be used in compositions according to the invention as solubilisers, or as cleansing agents or foam boosters. Many different classes of surfactant may be suitable for inclusion in the composition according to the invention, and these will be readily apparent to those skilled in the art. Examples of suitable surfactants include anionic surfactants (e.g., sodium laureth sulphate, non-ionic surfactants (e.g., cocoglucoside) cationic surfactants and/or amphoteric surfactants (e.g., cocoamidoproyl betaine). Polyethylene glycol ethers of alcohols such as isocetyl alcohol (e.g., Isoceteth-20), isostearyl alcohol (e.g., Isosteareth-20), cetyl alcohol (e.g., Ceteth-20), oleyl alcohol (e.g., Oleth-20) and cetearyl alcohol (e.g., Ceteareth-20).

d) Preservatives—ingredients which prevent or retard microbial growth and thus protect the composition from spoilage. Examples of preservatives include such as propylparaben, bronopol, sodium dehydroacetate, polyhexamethylenebiguanide hydrochloride, isothiazolone and diazolidinylurea.

e) Chelating agents or sequestering agents (sequestrants)—ingredients that have the ability to complex with and inactivate metallic ions in order to prevent their adverse effects on the stability or appearance of the composition, as described above. Examples of chelating agents are ethylenediamine tetraacetic acid and its salts, notably the dipotassium and especially the disodium or tetrasodium salt.

f) Abrasives—ingredients used to assist in the removal of unwanted tissue or foreign materials from the skin during application of the composition. Abrasives commonly comprise fine solid particles. Examples of suitable abrasives are polyethylene beads and aluminium oxide.

g) opacifying agents such as clays (e.g., kaolin and bentonite) as well as titanium dioxide.

h) pH adjusters—ingredients used to control the pH of the composition. Examples of pH adjusters are inorganic salts such as sodium hydroxide, and organic bases such as triethanolamine and arginine.

i) Conditioning agents, for example distearyldimonium chloride.

j) Perfumes and colourings.

The composition according to the invention may be applied and left on the skin to have the desired therapeutic effect, or it may be applied and then rinsed off, for example with water for surfactant based formulations. The composition may be applied with the aid of a fibrous material, for example a pad or a wipe.

According to another aspect of the invention, there is provided an article comprising a fibrous substrate, for example a material in the form of a pad or a wipe, impregnated with a skincare composition comprising salicylic acid or a salt thereof and at least 2 actives selected from the group consisting of lactic acid or a salt thereof; glycyrrhizinic acid or a salt or derivative thereof bisabolol; cetylhydroxyproline palmitamide; allantoin; niacinamide; and, and *Epilobium angustifolium* extract.

The fibrous material may be used to apply the composition onto the skin.

Suitable fibrous materials include cellulose or cotton fibres or a mixture thereof. The fibrous material may be impregnated with the composition as a wet wipe which is arranged for immediate use to apply the skincare composition of the present invention to the skin of the user. Alternatively, the fibrous material may be impregnated with the skincare composition and dried to form a dry wipe which requires to be wetted, for example with water, before it can be used.

According to a further aspect of the invention, there is provided method for the prophylactic or remedial treatment of acne, which method comprises the topical application to the skin of a patient of a skincare composition comprising salicylic acid or a salt thereof and at least 2 of the list comprising lactic acid or a salt thereof; glycyrrhizinic acid or a salt and their derivatives, bisabolol; cetylhydroxyproline palmitamide; allantoin; niacinamide; and *Epilobium angustifolium* extract.

It will be appreciated that the method according to this aspect of the invention may be a therapeutic method, but will often be a primarily cosmetic method, the objective of which is to reduce or eliminate externally visible, and often unsightly, symptoms of acne vulgaris.

In a yet further aspect of the invention, there is provided the use of salicylic acid and at least 2 actives selected from the group consisting of lactic acid (or salts thereof); glycyrrhizinic acid (or salts or derivatives thereof); bisabolol; cetylhydroxyproline palmitamide; allantoin; niacinamide and *Epilobium angustifolium* in the manufacture of a composition for the prophylactic or remedial treatment of acne by topical application of the composition to the skin.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

The invention will now be described in greater detail, by way of illustration only, with reference to the following Examples.

Example 1: Serum
Example 2: Clear gel scrub
Example 3: Pearlised Gel Scrub
Example 4: Wash/mask
Example 5: Wash/mask
Example 6: Hydro alcoholic gel
Example 7: Cream Scrub
Example 8: Foaming Cream Scrub The composition of each of these examples is shown fully in the following Tables 1-8.

Example 1

| Trade Name | % w/w in Formula | Function | EU INCI Name | % w/w in final formula |
|---|---|---|---|---|
| Purified water | QS 100 | Solvent | Aqua | to100% |
| Dissolvine Na2 | 0.05 | Sequestrant | Disodium EDTA | 0.05000 |
| Carbopol Ultrez 20 | 0.60 | Thickener | | 0.60000 |
| Veegum Ultra | 0.25 | Viscosity control (Thickener) | Magnesium Aluminum Silicate | 0.24250 |
| | | | CI 77891 | 0.00750 |
| Keltrol RD | 0.75 | Emulsion stabilising/ Viscosity control | Xanthan Gum | 0.75000 |
| Titanium dioxide Ph Eur | 0.20 | pigment | CI 77891 | 0.20000 |
| Eutanol G | 4.50 | Emollient | Octyldodecanol | 4.50000 |
| Arlamol HD | 1.50 | Emollient | Isohexadecane | 1.50000 |
| Silfar 100 | 2.00 | Skin conditioning | Dimethicone | 2.00000 |
| Salicylic acid | 2.00 | Keratolytic active | Salicylic Acid | 2.00000 |
| DENATURED ETHANOL SDA-40B 200 PROOF | 4.80 | Solvent | Alcohol Denat. (Ethyl Alcohol) | 4.79376 |
| | | Denaturant | Denatonium Benzoate | 0.00003 |
| | | Denaturant | Tert-Butyl alcohol | 0.00624 |
| SEPIGEL 305 | 2.0000 | Emulsion stabilising/ Viscosity control | Aqua | 0.71167 |
| | | | Polyacrylamide | 0.80000 |
| | | | C13-14 Isoparaffin | 0.37833 |
| | | | Laureth-7 | 0.11000 |
| CLEARLY FRESH FRAGRANCE | 0.2000 | Fragrance | Benzyl salicylate | 0.01844 |
| | | | Limonene | 0.00689 |
| | | | Parfum | 0.20000 |
| Sodium hydroxide 30% soln | 2.35 | Buffering agent | Aqua | 1.64500 |
| | | | Sodium hydroxide | 0.70500 |
| Purasal S/HQ 60 | 3.33 | moisturiser, skin lightener, anti-inflammatory | Aqua | 1.332 |
| | | | Sodium Lactate | 1.99800 |
| Symrepair | 0.50 | Anti-inflammatory, wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Nicotinamide | 2.00 | skin lightening, anti-inflammatory | Niacinamide | 2.00000 |
| Dipotassium Glycyrrhizate | 0.10 | anti-inflammatory/ skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 2

| Trade Name | % w/w in Formula | Function | EU INCI Name | % w/w in final formula |
|---|---|---|---|---|
| Purified Water | To 100% | Solvent | Aqua | to 100% |
| Carbopol Ultrez 20 | 1.3 | Suspending Agent | Acrylates/C10-30 Alkyl Acrylate Crosspolymer | 1.3 |
| Dissolvine Na2 | 0.1 | Sequestring Agent | Disodium EDTA | 0.1 |
| Glycerin | 8 | Humectant | Glycerin | 8 |
| Sorbitol | 2 | Humectant | Sorbitol | 1.40 |
| | | | Aqua | 0.60 |
| Empicol ESB3/M6 | 20 | Surfactant | Aqua | 14.37 |
| | | | Sodium Laureth Sulfate | 5.40 |
| | | | Sodium Hydroxide | 0.2 |
| Salicylic Acid | 2 | Active | Salicylic Acid | 2 |
| Cocoglucoside | 4.8 | Surfactant | Aqua | 2.352 |
| | | | Cocoglucoside | 2.544 |
| Tego Betaine | 6.9 | Surfactant | Cocamidopropyl Betaine | 2.553 |
| | | | Aqua | 3.726 |
| | | | Sodium Chloride | 0.5037 |
| Perfume Clearly Fresh | 0.25 | Fragrance | Parfum | 0.25 |
| | | | Limonene | 0.010329 |
| | | | Benzyl Salicylate | 0.023055 |
| Sodium Hydroxide | 3 | pH Adjuster | Sodium Hydroxide | 0.9 |
| | | | Aqua | 2.1 |
| Aluminium Oxide | 1.2 | Exfoliating Beads | Alumina | 1.2 |
| Cotahylene HO 1681 | 1 | Exfoliating Beads | Polyethylene | 1 |
| Gotalene Green | 0.2 | Exfoliating Beads | Polyethylene + COLOUR (TBD) | 0.2 |
| Genamin PQ 43 | 1 | Skin Conditioner | Aqua | 0.85 |
| | | | Polyquaternium 43 | 0.15 |
| FD&C Yellow 6 | 0.001 | Colourant | CI 15985 | 0.001 |
| FD & C Blue 1 | 0.002 | Colourant | CI 42090 | 0.002 |
| Purasal S/HQ 60 | 3.33 | Moisturiser, Skin lightener, Anti-inflammatory | Aqua | 1.3320 |
| | | | Sodium Lactate | 2.0000 |
| Nicotinamide | 2.00 | Skin lightening, Anti-inflammatory | Niacinamide | 2.0000 |
| Dipotassium Glycyrrhizate | 0.10 | Skin lightening, Anti-inflammatory | Dipotassium Glycyrrhizate | 0.1000 |
| SymRepair | 0.50 | Anri-inflammatory, Wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Allantoin | 0.50 | Anti-inflammatory | Allantoin | 0.5000 |
| Canadian Willowherb | 0.50 | Anti-inflammatory | *Epilobium angustifolium* | 0.0100 |

Example 3

| Trade Name | % w/w in Formula | Function | EU INCI Name | % w/w in final formula |
|---|---|---|---|---|
| Purified Water | To 100% | Solvent | Aqua | To 100% |
| Carbopol Ultrez 20 | 1.4 | Suspending Agent | Acrylates/C10-30 Alkyl Acrylate Crosspolymer | 1.4 |
| Dissolvine Na2 | 0.1 | Sequestring Agent | Disodium EDTA | 0.1 |
| Glycerin | 8 | Humectant | Glycerin | 8 |
| Polyquaternium 43 | 0.7 | Conditioning Agent | Polyquaternium 43 | 0.105 |
| | | | Aqua | 0.595 |
| Cocoglucoside | 4.8 | Surfactant | Aqua | 2.352 |
| | | | Cocoglucoside | 2.544 |

-continued

| Trade Name | % w/w in Formula | Function | EU INCI Name | % w/w in final formula |
|---|---|---|---|---|
| Tego Betaine | 6.9 | Surfactant | Cocamidopropyl Betaine | 2.553 |
| | | | Aqua | 3.726 |
| | | | Sodium Chloride | 0.5037 |
| Glycol Distearate | 2.5 | Pearlising Agent | Aqua | 1.625 |
| | | | Glycol Distearate | 0.25 |
| | | | Laureth-4 | 0.25 |
| | | | Cocamidopropyl Betaine | 0.25 |
| | | | Citric Acid | 0.125 |
| Empicol ESB3/M6 | 26.7 | Surfactant | Aqua | 19.18395 |
| | | | Sodium Laureth Sulfate | 7.209 |
| | | | Sodium Hydroxide | 0.267 |
| Salicylic Acid | 2 | Active | Salicylic Acid | 2 |
| Sodium Hydroxide | 3 | pH Adjuster | Sodium Hydroxide | 0.9 |
| | | | Aqua | 2.1 |
| Perfume Clearly Fresh | 0.2 | Fragrance | Parfum | 0.2 |
| | | | Benzyl Salicylate | 0.027666 |
| | | | Limonene | 0.006886 |
| Aluminium Oxide | 2.2 | Exfoliating | Alumina | 2.2 |
| Coathylene HO1681 | 2 | Exfoliating | Polyethylene | 2 |
| Gotalene Green | 0.2 | Exfoliating | Polyethylene (+CI TBD) | 0.2 |
| FD & C Yellow No. 6 | 0.0015 | Colour | Cl 15985 | 0.0015 |
| Blue No. 1 FD&C | 0.00225 | Colour | Cl 42090 | 0.00225 |
| Purasal S/HQ 60 | 3.33 | Moisturiser, Skin lightener, Anti-inflammatory | Aqua | 1.3320 |
| | | | Sodium Lactate | 2.0000 |
| Nicotinamide | 2.00 | Skin lightening, Anti-inflammatory | Niacinamide | 2.0000 |
| Dipotassium Glycyrrhizate | 0.10 | Skin lightening, Anti-inflammatory | Dipotassium Glycyrrhizate | 0.1000 |
| SymRepair | 0.50 | Anti-inflammatory, Wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Allantoin | 0.50 | Anti-inflammatory | Allantoin | 0.5000 |
| Canadian Willowherb | 0.50 | Anti-inflammatory | *Epilobium angustifolium* | 0.0100 |

Example 4

| Trade Name | % w/w in Formula | Function | EU INCI Name | % w/w in final formula |
|---|---|---|---|---|
| Purified Water | to 100% | Solvent | Aqua | To 100% |
| Dissolvine Na2 | 0.01 | Sequestring Agent | Disodium EDTA | 0.0100 |
| Glycerin | 8.00 | Humectant | Glycerin | 8.0000 |
| Sodium Hydroxide 30% Solution | 1.25 | pH Adjuster | Aqua | 0.8750 |
| | | | Sodium Hydroxide | 0.3750 |
| Keltrol RD | 0.20 | Emulsion Stabiliser/Thickener | Xanthan Gum | 0.20 |
| Veegum Ultra | 0.20 | Emulsion Stabiliser/Thickener | Magnesium Aluminium Silicate | 0.194 |
| | | | CI77891 | 0.006 |
| Dehydol LS3 | 4.00 | Emulsifier/Surfactant | Laureth-3 | 4.0000 |
| Lanette 1665 | 8.00 | Emulsifier | Cetearyl Alcohol | 8.0000 |

| Trade Name | % w/w in Formula | Function | EU INCI Name | % w/w in final formula |
|---|---|---|---|---|
| Salicylic Acid | 2.00 | Active | Salicylic Acid | 2.0000 |
| Hostopan SCI 85G | 10.00 | Surfactant | Sodium Cocoyl Isethionate | 8.5000 |
| | | Emollient/Emulsifying/ Surfactant | Coconut Acid | 1.0000 |
| | | Antistatic/Hair conditioning/Cleansing Solvent | Sodium Isethionate | 0.4000 |
| | | | Aqua | 0.0010 |
| Empicol ESB3/M6 | 4.00 | Surfactant | Aqua | 2.8740 |
| | | | Sodium Laureth Sulfate | 1.080 |
| | | | Sodium Hydroxide | 0.040 |
| Tego glycinate 818M | 3.50 | Non-ionic surfactant | Sodium cocoamphoacetate | 1.05000 |
| | | | Aqua | 2.17000 |
| Kaolin | 6.00 | Clay | Hydrated Aluminium Silicate | 6.0000 |
| Dry Flo PC | 2.00 | Oil Absorber | Aluminum Starch Octenylsuccinate | 2.0000 |
| Titanium Dioxide Ph Eur | 2.00 | Opacifier | CI77891 | 2.0000 |
| Perfume Clearly Fresh | 0.30 | Fragrance | Parfum | 0.3000 |
| | | | Benzyl Salicylate | 0.0277 |
| | | | Limonene | 0.0103 |
| Phenonip | 0.30 | Preservative | Phenoxyethanol | 0.2178 |
| | | | Ethyl paraben | 0.045 |
| | | | Propyl paraben | 0.012 |
| | | | Isobutyl paraben | 0.012 |
| | | | Butyl Paraben | 0.006 |
| | | | Methyl Paraben | 0.006 |
| Bentonite | 3.00 | Sebum Absorber | Bentonite | 3.0000 |
| Purasal S/HQ 60 | 3.33 | Moisturiser, Skin lightener, Anti-inflammatory | Aqua | 1.3320 |
| | | | Sodium Lactate | 2.0000 |
| Nicotinamide | 2.00 | Skin lightening, Anti-inflammatory | Niacinamide | 2.0000 |
| Dipotassium Glycyrrhizate | 0.10 | Skin lightening, Anti-inflammatory | Dipotassium Glycyrrhizate | 0.1000 |
| SymRepair | 0.50 | Anti-inflammatory, Wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Allantoin | 0.50 | Anti-inflammatory | Allantoin | 0.5000 |
| Canadian Willowherb | 0.50 | Anti-inflammatory | *Epilobium angustifolium* | 0.0100 |

Example 5

| Trade Name | % w/w in Formula | Function | EU INCI Name | % w/w in final formula |
|---|---|---|---|---|
| Purified Water | To 100% | Solvent | Aqua | To 100% |
| Dissolvine Na2 | 0.05 | Sequestring Agent | Disodium EDTA | 0.05 |
| Glycerin | 7 | Humectant | Glycerin | 7.00 |
| Polyquaternium 43 | 0.3 | Conditioning Agent | Polyquaternium 43 | 0.045 |
| | | | Aqua | 0.255 |
| Keltrol RD | 0.3 | Emulsion Stabiliser/ Thickener | Xanthan Gum | 0.30 |
| Veegum Ultra | 0.3 | Emulsion Stabiliser/ Thickener | Magnesium Aluminium Silicate | 0.291 |
| | | | CI77891 | 0.009 |
| Butylene Glycol | 3 | Humectant | Butylene Glycol | 3.00 |
| Salicylic Acid | 2 | Active | Salicylic Acid | 2.00 |
| Empicol | 13.3 | Surfactant | Aqua | 9.5561 |

-continued

| Trade Name | % w/w in Formula | Function | EU INCI Name | % w/w in final formula |
|---|---|---|---|---|
| ESB3/M6 | | | Sodium Laureth Sulfate | 3.591 |
| | | | Sodium Hydroxide | 0.133 |
| Cocoglucoside 50% | 3.2 | Surfactant | Aqua | 1.568 |
| | | | Cocoglucoside | 1.696 |
| Tego Betaine | 4.6 | Surfactant | Cocamidopropyl Betaine | 1.702 |
| | | | Aqua | 2.484 |
| | | | Sodium Chloride | 0.3358 |
| Phenonip | 0.3 | Preservative | Phenoxyethanol | 0.2178 |
| | | | Ethyl paraben | 0.045 |
| | | | Propyl paraben | 0.012 |
| | | | Isobutyl paraben | 0.012 |
| | | | Butyl Paraben | 0.006 |
| | | | Methyl Paraben | 0.006 |
| Sodium Hydroxide | 1.25 | pH Adjuster | Sodium Hydroxide | 0.38 |
| | | | Aqua | 0.88 |
| Kaolin | 8 | Clay | Hydrated Aluminium Silicate | 8.00 |
| Bentonite | 4 | Sebum Absorber | Bentonite | 4.0000 |
| Titanium Dioxide | 2 | Opacifier | CI77891 | 2.0000 |
| Fragrance Clearly Fresh | 0.2 | Fragrance | Parfum | 0.2000 |
| | | | Benzyl Salicylate | 0.0277 |
| | | | Limonene | 0.0069 |
| Structure XL | 2 | Thickener/foam boosrter | Hydroxypropyl Starch Phosphate | 2.0000 |
| Structure Plus | 0.4 | Thickener | Acrylates/ Aminoacrylates/ C10-30 Alkyl PEG-20 Itaconate Copolymer | 0.0800 |
| | | | Aqua | 0.3160 |
| | | | Phenoxyethanol | 0.00288 |
| | | | Methyl Paraben | 0.00064 |
| | | | Ethyl Paraben | 0.00016 |
| | | | Propyl Paraben | 0.00008 |
| | | | Butyl Paraben | 0.00016 |
| | | | Isobutyl Paraben | 0.00008 |
| Blue No. 1 FD&C | 0.0018 | Colour | Cl 42090 | 0.0018 |
| Purasal S/HQ 60 | 3.33 | Moisturiser, Skin lightener, Anti-inflammatory | Aqua | 1.332 |
| | | | Sodium Lactate | 1.998 |
| Nicotinamide | 2 | Skin lightening, Anti-inflammatory | Niacinamide | 2.000 |
| Dipotassium Glycyrrhizate | 0.1 | Skin lightening, Anti-inflammatory | Dipotassium Glycyrrhizate | 0.100 |
| SymRepair | 0.5 | Anri-inflammatory, Wound healing | Hexyldecanol | 0.420 |
| | | | Bisabolol | 0.025 |
| | | | Cetylhydroxyproline Palmitamide | 0.025 |
| | | | Stearic Acid | 0.025 |
| | | | *Brassica Campestris* Sterols | 0.005 |
| Allantoin | 0.5 | Anti-inflammatory | Allantoin | 0.5 |
| Canadian Willowherb | 0.50 | Anti-inflammatory | *Epilobium angustifolium* | 0.0100 |

Example 6

| Trade Name | % w/w in Formula | Function | EU INCI Name | % w/w in final formula |
|---|---|---|---|---|
| Purified water | Qs 100 | Solvent | Aqua | To 100% |
| Jaguar HP 105 | 1.20 | Thickener | Hydroxypropyl Guar | 1.12680 |
| | | | Aqua | 0.10800 |
| | | | Proteins | 0.01200 |
| | | | Ashes | 0.01920 |

-continued

| Trade Name | % w/w in Formula | Function | EU INCI Name | % w/w in final formula |
|---|---|---|---|---|
| Timiron Silk Green | 0.20 | pearlising agent | CI77891 | 0.14200 |
| | | | Mica | 0.07400 |
| | | | Tin oxide | 0.00200 |
| Salicylic acid | 2.00 | Keratolytic active | Salicylic Acid | 2.00000 |
| Tween 20 | 2.50 | surfactant | Polysorbate 20 | 2.50000 |
| DENATURED ETHANOL | 27.00 | Solvent | Alcohol Denat. (Ethyl Alcohol) | 26.96490 |
| SDA-40B 200 PROOF | | Denaturant | Denatonium Benzoate | 0.00016 |
| | | Denaturant | Tert-Butyl alcohol | 0.03510 |
| Sodium hydroxide 30% soln | 2.00 | Buffering agent | Aqua | 1.40000 |
| | | | Sodium hydroxide | 0.60000 |
| CLEARLY FRESH FRAGRANCE | 0.2000 | Fragrance | Benzyl salicylate | 0.01844 |
| | | | Limonene | 0.00689 |
| | | | Parfum | 0.00000 |
| Purasal S/HQ 60 | 3.33 | moisturiser, skin lightener, anti-inflammatory | Aqua | 1.332 |
| | | | Sodium Lactate | 1.99800 |
| Symrepair | 0.50 | Anti-inflammatory, wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Nicotinamide | 2.00 | skin lightening, anti-inflammatory | Niacinamide | 2.00000 |
| Dipotassium Glycyrrhizate | 0.10 | anti-inflammatory/skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 7

| Trade Name | % w/w in Formula | Function | EU INCI Name | % w/w in final formula |
|---|---|---|---|---|
| None | To 100% | Solvent | Aqua | To 100% |
| DISSOLVINE NA2 | 0.01000 | Sequestrant | Disodium EDTA | 0.01000 |
| Veegum ultra | 0.25000 | Emulsion stabiliser/Thickener | Magnesium Aluminium Silicate | 0.24250 |
| | | | CI77891 | 0.00750 |
| Keltrol RD | 0.50000 | Emulsion stabiliser/Thickener | Xanthan Gum | 0.25 |
| Glycerin 99.7% USP | 3.00000 | Humectant | Glycerin | 3.00000 |
| Arlamole E | 2.00000 | Emollient | PPG-15 Stearyl Ether | 2.00000 |
| | | | Stearyl Alcohol | 3 |
| SALICYLIC ACID USP | 2.00000 | Keratolytic | Salicylic Acid | 2.00000 |
| Varisoft TA 100 | 1.50000 | Skin Conditioning | Distearyldimonium Chloride | 1.44000 |
| | | | Aqua | 0.06000 |
| | | | Sodium Chloride | 0.00225 |
| Tego Alkanol 16 | 1.00000 | Emollient | Myristyl Alcohol | 0.02500 |
| | | | Cetyl Alcohol | 1.00000 |
| Birj 721 | 0.50000 | Emulsifier | Steareth-21 | 0.49000 |
| | | | Aqua | 0.01000 |
| | | | Stearyl Alcohol | 0.03360 |
| | | | Arachidyl Alcohol | 0.08400 |
| | | | Behenyl Alcohol | 0.33600 |
| Tego Alkanol S2 | 0.25000 | Emilsifier | Steareth-2 | 0.25000 |
| Stepanol-WA extra PCA (SLS) | 3.57000 | Surfactant | Aqua | 2.53470 |
| | | | Sodium Lauryl Sulfate | 1.07100 |
| | | | Lauryl Alcohol | 0.04641 |
| | | | Sodium Sulfate | 0.02499 |

-continued

| Trade Name | % w/w in Formula | Function | EU INCI Name | % w/w in final formula |
|---|---|---|---|---|
| Tego Betain A 16 | 6.67000 | Surfactant | Aqua | 3.60180 |
| | | | Cetyl Betaine | 2.13440 |
| | | | Alcohol | 0.66700 |
| | | | Sodium Chloride | 0.46690 |
| Clearly Fresh E0525379 | 0.35000 | Fragrance | Benzyl Salicylate | 0.03228 |
| | | | Limonene | 0.01205 |
| | | | Parfum | 0.35000 |
| Aluminium oxide F100 | 8.00000 | Abrasive agent | Alumina | 8.00000 |
| Purasal S/HQ 60 | 3.33 | Moisturiser, skin lightener, anti-inflammatory | Aqua | 1.333 |
| | | | Sodium Lactate | 2.00000 |
| SymRepair | 0.50 | Anti-inflammatory, wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Nicotinamide | 2.00 | Skin lightening, anti-inflammatory | Niacinamide | 2.00000 |
| Dipotassium Glycyrrhizate | 0.10 | Anti-inflammatory/ skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 8

| Trade Name | % w/w in Formula | Function | EU INCI Name | % w/w in final formula |
|---|---|---|---|---|
| None | To 100% | Solvent | Aqua | to 100% |
| DISSOLVINE NA2 | 0.05000 | Sequestrant | Disodium EDTA | 0.05000 |
| Carbopol ultrez 20 | 0.30000 | thickener | Acrylates/C10-30 Alkyl Acrylate Crosspolymer | 0.30000 |
| | | | Ethyl Acetate | 0.00135 |
| | | | Cyclohexane | 0.00135 |
| Glycerin 99.7% USP | 3.00000 | Humectant | Glycerin | 3.00000 |
| FD&C Blue No. 1 Granules | 0.00045 | Colorant | CI 42090 | 0.00042 |
| FD&C Yellow 6 | 0.00030 | Colorant | CI 15985 | 0.00030 |
| Hostapon SCI 85G | 10.00000 | Surfactant | Sodium Cocoyl Isethionate | 8.50000 |
| | | | Coconut Acid | 1.00000 |
| | | | Sodium Isethionate | 0.40000 |
| | | | Aqua | 0.10000 |
| Genapol LA030 | 3.00000 | Emulsifying/ Surfactant | Laureth-3 | 3.00000 |
| Tego Alkanol 16 | 6.00000 | Emollient | Myristyl Alcohol | 0.15000 |
| | | | Cetyl Alcohol | 6.00000 |
| SALICYLIC ACID USP | 2.00000 | Keratolytic | Salicylic Acid | 2.00000 |
| Empicol ESB3/M6 | 9.26000 | Anionic Surfactant | Sodium Laureth Sulfate | 2.54650 |
| | | | Aqua | 6.80610 |
| Sodium Hydroxide 30% | 1.25000 | Buffering agent | Sodium hydroxide | 0.37500 |
| | | | Aqua | 1.12500 |
| Tego glycinate 818 M | 6.13000 | Non-ionic surfactant | Sodium cocoamphoacetate | 1.83900 |
| | | | Aqua | 3.80060 |
| Clearly Fresh E0525379 | 0.35000 | Fragrance | Benzyl Salicylate | 0.03228 |
| | | | Limonene | 0.01205 |
| | | | Parfum | 0.35000 |
| Genamin PQ 43 | 0.10000 | Conditioning agent | Polyquaternium 43 | 0.08500 |
| | | | Aqua | 0.01500 |

-continued

| Trade Name | % w/w in Formula | Function | EU INCI Name | % w/w in final formula |
|---|---|---|---|---|
| Aluminium oxide F100 | 8.00000 | Abrasive agent | Alumina | 8.00000 |
| Parabeads green | 0.50000 | Exfoliant | Mycrocristalline wax | 0.48995 |
|  |  |  | CI 77289 | 0.01000 |
|  |  |  | Tocopherol (Processing aid) | 0.00005 |
| Purasal S/HQ 60 | 3.33 | Moisturiser, skin lightener, anti-inflammatory | Aqua | 1.33300 |
|  |  |  | Sodium Lactate | 2.00000 |
| SymRepair | 0.50 | Anti-inflammatory, wound healing | Hexyldecanol | 0.42000 |
|  |  |  | Bisabolol | 0.02500 |
|  |  |  | Cetylhydroxyproline Palmitamide | 0.02500 |
|  |  |  | Stearic Acid | 0.02500 |
|  |  |  | *Brassica Campestris* Sterols | 0.00500 |
| Nicotinamide | 2.00 | Skin lightening, anti-inflammatory | Niacinamide | 2.00000 |
| Dipotassium Glycyrrhizate | 0.10 | Anti-inflammatory/skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 9

| Supplier | Trade Name | % w/w in Formula | Function | EU INCI Name | % w/w in raw material | % w/w in final formula |
|---|---|---|---|---|---|---|
|  | Purified water | 73.12 | Solvent | Aqua | 100 | 73.12 |
| Akzo Nobel | Dissolvine Na2 | 0.05 | Sequestrant | Disodium EDTA | 100 | 0.05 |
| Noveon | Carbopol Ultrez 20 | 0.60 | Thickener | Acrylates/C10-30 Alkyl Acrylate crosspolymer | 100 | 0.6 |
| RT Vanderbilt Co | Veegum Ultra | 0.25 | Viscosity control (Thickener) | Magnesium Aluminum Silicate | 97 | 0.2425 |
|  |  |  |  | Titanium Dioxide | 3 | 0.0075 |
| CP Kelco | Keltrol RD | 0.60 | Emulsion stabilising Viscosity control | Xanthan Gum | 100 | 0.6 |
| sensient | Titanium dioxide Ph Eur | 0.20 | pigment | Titanium Dioxide | 100 | 0.2 |
| Cognis | Eutanol G | 4.50 | Emollient | Octyldodecanol | 100 | 4.5 |
| Croda | Arlamol HD | 1.50 | Emollient | Isohexadecane | 100 | 1.5 |
| Wacker | Silfar 100 | 2.00 | Skin conditioning | Dimethicone | 100 | 2.0 |
| Rhodia | Salicylic acid | 2.00 | Keratolytic active | Salicylic Acid | 100 | 2.0 |
| MGP Ingredientes | Denatured Ethanol | 4.80 | Solvent | Alcohol Denat. (Ethyl Alcohol) | 99.87 | 4.79376 |
| Seppic | SEPIGEL 305 | 2.0 | Emulsion stabilising/Viscosity control | Water | 35.583 | 0.71167 |
|  |  |  |  | Polyacrylamide | 40 | 0.8 |
|  |  |  |  | C13-14 Isoparaffin | 18.917 | 0.37833 |
|  |  |  |  | Laureth-7 | 5.5 | 0.11 |
| Mane | CLEARLY FRESH FRAGRANCE | 0.20 | Fragrance | Benzyl salicylate | 9.222 | 0.01844 |
|  |  |  |  | Limonene | 3.443 | 0.00689 |
|  |  |  |  | Fragrance | 100 | 0.2 |
| Univar | Sodium hydroxide 30% soln | 2.35 | Buffering agent | Water | 70 | 1.645 |
|  |  |  |  | Sodium hydroxide | 30 | 0.705 |
| Purac | Purasal S/HQ 60 | 3.33 | moisturiser, skin lightener, anti-inflammatory | Water | 40 | 1.332 |
|  |  |  |  | Sodium Lactate | 60 | 1.998 |

-continued

| Supplier | Trade Name | % w/w in Formula | Function | EU INCI Name | % w/w in raw material | % w/w in final formula |
|---|---|---|---|---|---|---|
| Symrise | Symrepair | 0.50 | Anti-inflammatory, wound healing | Hexyldecanol | 84 | 0.42 |
| | | | | Bisabolol | 5.0 | 0.025 |
| | | | | Cetylhydroxyproline Palmitamide | 5.0 | 0.025 |
| | | | | Stearic Acid | 5.0 | 0.025 |
| | | | | *Brassica Campestris* Sterols | 1.0 | 0.005 |
| Rona (S Black) | Nicotinamide | 2.00 | skin lightening, anti-inflammatory | Niacinamide | 100 | 2.0 |
| Jan Dekkar (Maurazen) | Dipotassium Glycyrrhizate | 0.05 | anti-inflammatory/ skin lightening | Dipotassium Glycyrrhizate | 100 | 0.05 |

Example 10

| Supplier | Trade Name | % w/w in Formula | Function | EU INCI Name | % w/w in raw material | % w/w in final formula |
|---|---|---|---|---|---|---|
| — | Purified Water | 56.55685 | Solvent | Aqua | 100 | 56.55685 |
| BASF | Trilon BD | 0.05 | Sequestering Agent | Disodium EDTA | 100 | 0.050 |
| P & G | Glycerin | 5.00 | Humectant | Glycerin | 100 | 5.00 |
| CP Kelco | Keltrol RD | 1.00 | Emulsion stabiliser/Thickener | Xanthan Gum | 100 | 1.00 |
| Rhodia | Salicylic Acid | 2.00 | Active | Salicylic Acid | 100 | 2.00 |
| Huntsman | Empicol ESB3/M6 | 10.70 | Surfactant | Sodium Laureth Sulfate | 27.5 | 2.9425 |
| | | | | Aqua | 73.5 | 7.8645 |
| Cognis | Cocoglucoside 50% | 1.00 | Surfactant | Aqua | 49 | 0.490 |
| | | | | Cocoglucoside | 53 | 0.530 |
| Evonik | Tego Betaine | 1.31 | Surfactant | Cocamidopropyl Betaine | 37 | 0.485 |
| | | | | Aqua | 54 | 0.707 |
| | | | | Sodium Chloride | 7.3 | 0.0956 |
| Brenntag | Sodium Hydroxide | 1.20 | pH Adjuster | Sodium Hydroxide | 30 | 0.36 |
| | | | | Aqua | 70 | 0.840 |
| Brenntag | Kaolin | 6.00 | Clay | Hydrated Aluminium Silicate | 100 | 6.00 |
| Brenntag | Bentonite | 6.00 | Sebum Absorber | Bentonite | 100 | 6.00 |
| Huntsman | Titanium Dioxide | 3.00 | Opacifier | CI77891 | 100 | 3.00 |
| Mane | Fragrance Clearly Fresh | 0.30 | Fragrance | Benzyl Salicylate | 9.222 | 0.03 |
| | | | | Limonene | 3.443 | 0.01 |
| | | | | Parfum | 100 | 0.30 |
| Sun Chem | Blue No. 1 | 0.0026 | Colour | CI 42090 | 100 | 0.00260 |
| Sun Chem | Yellow No. 6 | 0.00055 | Colour | CI 15985 | 100 | 0.00055 |
| Purac | Purasal S/HQ 60 | 3.33 | Moisturiser, Skin lightener, Anti-inflammatory | Aqua | 40 | 1.33 |
| | | | | Sodium Lactate | 60 | 2.00 |
| Rona (S Black) | Nicotinamide | 2.00 | Skin lightening, Anti-inflammatory | Niacinamide | 100 | 2.00 |
| Jan Dekkar (Maurazen) | Dipotassium Glycyrrhizate | 0.05 | Skin lightening, Anti-inflammatory | Dipotassium Glycyrrhizate | 100 | 0.05 |
| Symrise | SymRepair | 0.50 | Anti-inflammatory, Wound healing | Hexyldecanol | 84 | 0.42 |
| | | | | Bisabolol | 5 | 0.03 |
| | | | | Cetylhydroxyproline Palmitamide | 5 | 0.03 |
| | | | | Stearic Acid | 5 | 0.03 |
| | | | | *Brassica Campestris* Sterols | 1 | 0.01 |

Example 11—In Vitro Testing (EpiDerm Skin Model)

| Material | MTT < 95% | IL-6 no PMA (pg/ml) | IL-6 + PMA (pg/ml) | TNFα no PMA (pg/ml) | TNFα + PMA (pg/ml) | IL-8 no PMA (pg/ml) | IL-8 no PMA (pg/ml) |
|---|---|---|---|---|---|---|---|
| Negative Control value | | | −0.371 | | 63.64 | | 996.8 |
| Positive control (hydrocortisone) | | | −4.358 | | −0.378 | | 48.5 |
| Nicotinamide (NA) | 96.8 | −4.294 | −2.712 | −0.171 | 40.202 | 47.54 | 1383.235 |
| Dipotassium glycyrrhizinate (GLYR) | 93.7 | −1.781 | 7.591 | −0.636 | 78.48 | 44.413 | 995.622 |
| Sodium Lactate (SLA) | 99.1 | 4.909 | 22.6 | 0.882 | 92.434 | 104.549 | 1368.319 |
| Symrepair (SYM) | 101.3 | −4.231 | 1.512 | −0.687 | 72.343 | 17.767 | 735.562 |
| Salicylic acid (SCA) | 103.2 | −1.445 | 6.159 | −0.068 | 12.265 | 72.757 | 362.253 |
| SCA + NA | 106.3 | −4.231 | −3.407 | −0.481 | 5.535 | 38.963 | 392.411 |
| GLYR + SCA + NA | 105.6 | −3.153 | −0.877 | −0.274 | 4.541 | 61.931 | 412.226 |
| NA + GLYR + SLA | 113.7 | −2.837 | 1.955 | −0.088 | 52.327 | 62.91 | 2513.021 |
| Example 9 (NA + GLYR + SLA + SCA) | 99.7 | −1.192 | 1.267 | −0.171 | 9.802 | 88.766 | 938.475 |

The purpose of the in vitro testing was to evaluate the potential anti-inflammatory action of compositions according to the present invention.

In vitro tests were carried out as follows:
take an irritant treated EpiDerm™ skin model. Initial inflammation was measured by the cytokine release after exposure to a single dose of irritant.
apply test compositions to the irritant treated EpiDerm skin
anti-inflammatory potential was then measured by reduction in cytokine release
specifically, the levels of cytokines TNF-α, IL-6 and IL-8 were measured to give a picture of the performance of the product across the lifecycle of an acne event or related skin inflammation.

Experimental design follows standard procedures, using phorbol-12-myristate 13-acetate (PMA) as irritant. Test samples were applied by pipette as solutions to the Epiderm tissue, and each sample was tested in triplicate against positive and negative controls. Anti-inflammatory activity measured by relative decrease in cytokine release in irritant-treated tissue compared to non-irritant treated tissue.

The separate active components of an example according to the invention were tested, along with some combinations in pairs and one combination lacking the salicylic acid. Where these actives were applied, they were in the same w/w ratio as in the example composition, example 9. The data shown in the table are the cytokine release values in pg/ml, wherein a lower figure shows a lower release rate of cytokines, i.e., a lower inflammation.

It will be seen that salicylic acid alone acts inter alia as an anti-inflammatory, but that unexpectedly it also acts with the combination of ingredients in the example according to the invention to reduce significantly the inflammatory behaviour of each of these ingredients. This synergistic behaviour is totally unexpected and permits the formulation of products according to the invention such as the one tested which have a broad range of active ingredients to deal with traumas arising from every stage in the lifecycle of a specific acne event or related skin inflammation.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims.

What is claimed is:

1. A cosmetic method for improving the appearance of skin afflicted by acne lesions, said method comprising reducing the redness of said lesions by the topical application of a skincare composition consisting of:
salicylic acid or a salt thereof in a concentration of 2 wt %;
glycyrrhizinic acid or a salt thereof in a concentration of 0.05 wt %;
cetylhydroxyproline palmitamide in a concentration of 0.025 wt %;
lactic acid or a salt thereof in a concentration of 1.998 wt %;
bisabolol in a concentration of 0.025 wt %;
niacinamide in a concentration of 2 wt %;
a chelating agent in a concentration of 0.01 wt % to 0.1 wt %;
a gelling/thickening agent in a concentration of 0.1 wt % to 5 wt %;
an emulsifier in a concentration of 0.75 wt % to 12 wt %;
a mixed solvent system comprising water and a co-solvent wherein the co-solvent is present in a concentration of 0 wt % to about 5 wt % and the water forms the remainder of the composition;
an emollient in a concentration of 0 wt % to 8 wt %;
a humectant or moisturizer in a concentration of 0 wt % to 10 wt %;
a surfactant in a concentration of 0 wt % to about 38 wt %;
a preservative in a concentration of 0 wt % to 0.3 wt %;
an abrasive in a concentration of 0 wt % to 8.5 wt %;
an opacifying agent in a concentration of 0 wt % to 15 wt %;
a pH adjuster in a concentration of 0 wt % to 3 wt %;

a conditioning agent in a concentration of 0 wt % to 1.5 wt %;
a perfume in a concentration of 0 wt % to 0.35 wt %; and
a coloring in a concentration of 0 wt % to 0.00315 wt %,
wherein the composition has a viscosity of from about 10,000 mPa/s to about 200,000 mPa/s.

2. The method as claimed in claim 1, wherein the pH of the skincare composition is in the range from 3.5 to 6.0.

3. The method as claimed in claim 1, wherein the skincare composition has the form of one of an aqueous solution surfactant wash, an oily solution surfactant wash, a dispersion, an emulsion, or a gel.

4. The method as claimed in claim 3, wherein the skincare composition has the form of an emulsion comprising an oil-in-water emulsion.

5. The method as claimed in claim 3, wherein the skincare composition has the form of a gel comprising an aqueous gel.

6. An article comprising a fibrous substrate configured for topical application of the skincare composition according to claim 1.

7. The article as claimed in claim 6, the fibrous substrate selected from the group consisting of cellulose fibers, cotton fibers, and a mixture thereof.

8. A method for the treatment of acne comprising:
topically applying a skincare composition according to claim 1 to the skin of a patient.

9. The method as claimed in claim 8, which is a cosmetic method.

10. The method as claimed in claim 8, which is a therapeutic method.

11. The use of the composition according to claim 1 in a composition for the treatment of acne by topical application of the composition to the skin.

12. A method for reducing irritancy associated with the topical application of a skincare composition comprising topical application of a skincare composition according to claim 1.

13. A cosmetic method for improving the appearance of skin afflicted by acne lesions comprising reducing the redness of lesions by the topical application of a skincare composition according to claim 1.

14. The method as claimed in claim 3, wherein the skincare composition has the form of an emulsion selected from the group consisting of an oil-in-water emulsion, a water-in-oil emulsion, and a microemulsion.

* * * * *